United States Patent [19]

Bareth

[11] Patent Number: 4,781,589

[45] Date of Patent: Nov. 1, 1988

[54] CLAMPING ARRANGEMENT, ESPECIALLY FOR DENTAL INSTRUMENTS

[75] Inventor: Erich Bareth, Ummendorf, Fed. Rep. of Germany

[73] Assignee: Kaltenbach & Voight GmbH & Co., Biberach an der Riss, Fed. Rep. of Germany

[21] Appl. No.: 879,916

[22] Filed: Jun. 30, 1986

[30] Foreign Application Priority Data

Jul. 25, 1985 [DE] Fed. Rep. of Germany ....... 3526684

[51] Int. Cl.⁴ .............................................. A61C 1/14
[52] U.S. Cl. .................................... 433/127; 433/128; 433/129; 433/122; 279/22; 279/30
[58] Field of Search ............... 433/127, 128, 129, 118, 433/122; 279/22, 30

[56] References Cited

U.S. PATENT DOCUMENTS

| | | | |
|---|---|---|---|
| 456,477 | 7/1891 | Coulson | 433/122 |
| 1,027,525 | 5/1912 | Corn | 279/22 |
| 2,135,933 | 11/1938 | Blair | 433/122 |
| 3,074,167 | 1/1963 | Turchi et al. | 433/129 |
| 3,637,050 | 1/1972 | Hoffmeister | 433/127 |

FOREIGN PATENT DOCUMENTS

| | | | |
|---|---|---|---|
| 0811250 | 6/1951 | Fed. Rep. of Germany | 433/127 |
| 0688136 | 2/1953 | United Kingdom | 433/127 |

Primary Examiner—John J. Wilson
Assistant Examiner—Adriene J. Lepiane
Attorney, Agent, or Firm—Scully, Scott, Murphy & Presser

[57] ABSTRACT

A clamping arrangement, especially for the clamping or gripping engagement of dental implements, consisting of a receiving sleeve which is rotatably supported in a handpiece and is connected with a rotary drive, which includes at least one rod-shaped elongated clamping element exerting a radially inwardly directed pressure against the shaft of the implement which is inserted into the receiving sleeve because of contact against an inclined track oriented perpendicular to the longitudinal axis of the clamping arrangement. The handpiece can pertain to a straight handpiece or to an angled handpiece (elbow) with an angled headpiece.

16 Claims, 2 Drawing Sheets

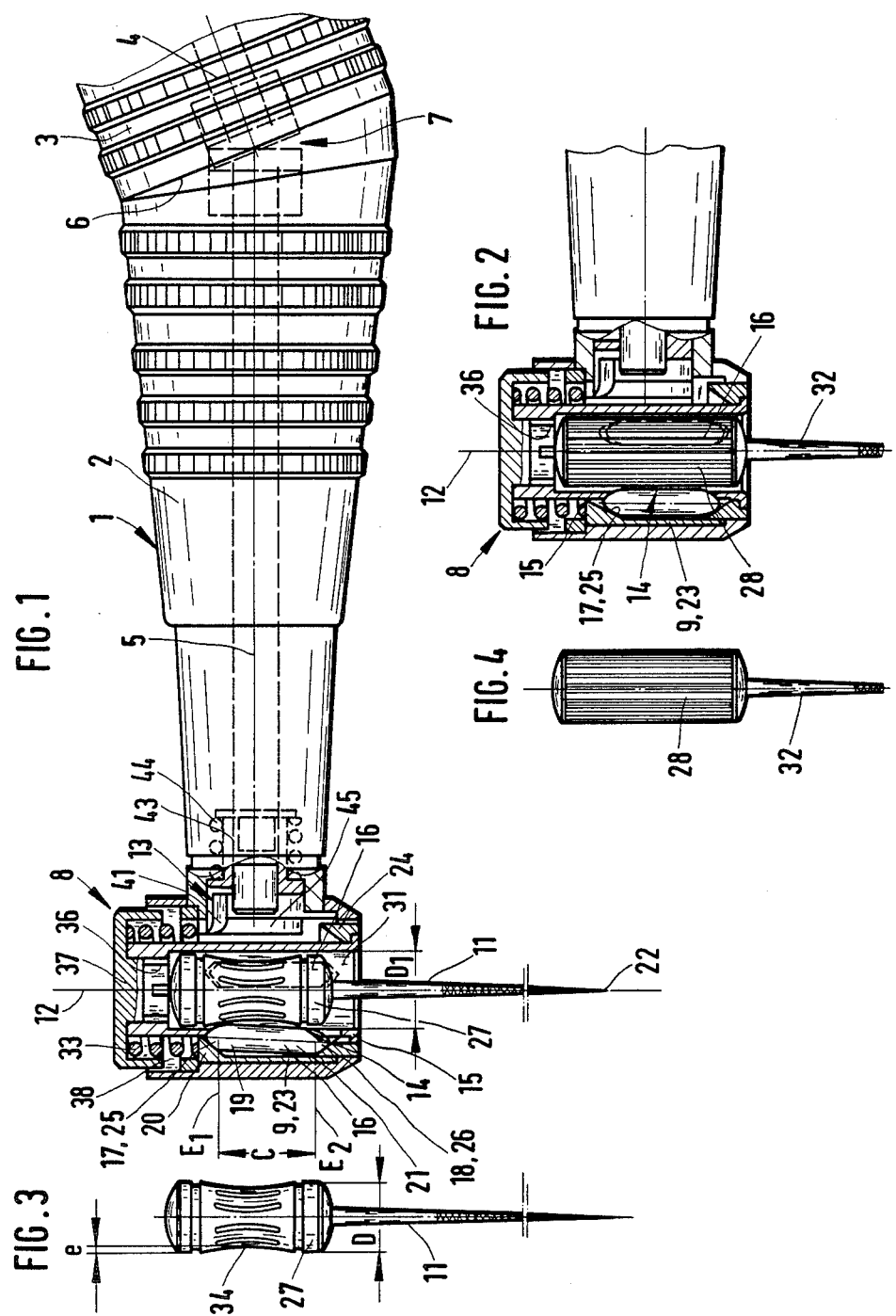

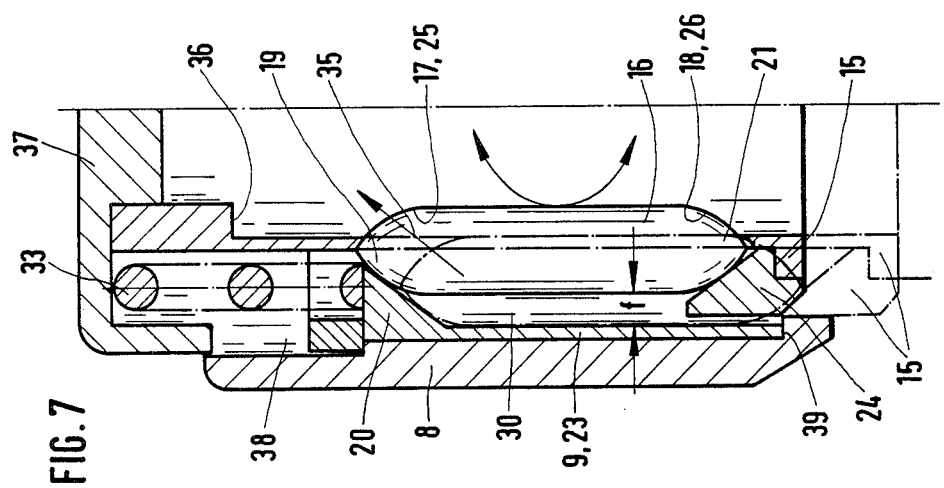
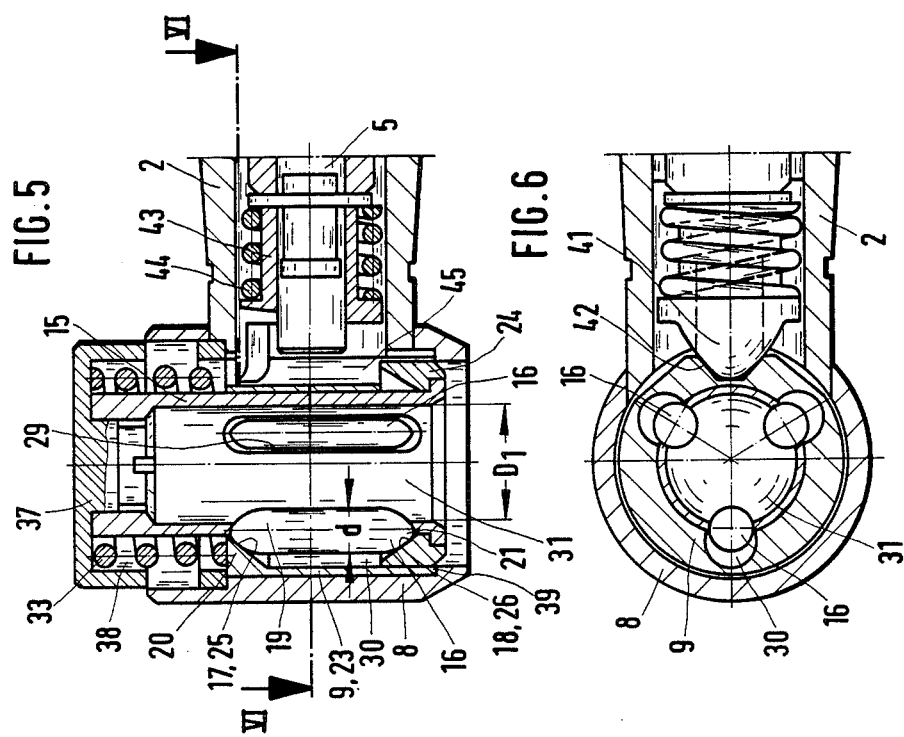

CLAMPING ARRANGEMENT, ESPECIALLY FOR DENTAL INSTRUMENTS

BACKGROUND OF THE INVENTION

1. Field of the Invention

The present invention relates to a clamping arrangement, especially for the clamping or gripping engagement of dental implements, including a receiving sleeve which is rotatably supported in a handpiece and is connected with a rotary drive, which includes at least one clamping element exerting a radially inwardly directed pressure against the shaft of the implement which is inserted into the receiving sleeve because of contact against an inclined track oriented perpendicular to the longitudinal axis of the clamping arrangement. The handpiece can pertain to a straight handpiece or to an angled handpiece (elbow) with an angled headpiece.

The invention is particularly adapted as a clamping arrangement for the clamping or gripping engagement of medical, and preferably dental implements.

2. Discussion of the Prior Art

A clamping arrangement of that type has become known from the disclosure of Swiss Pat. No. 581 463. In this known clamping arrangement, the clamping element is formed by a ball which is supported so as to be radially displaceable within a radial cutout in the receiving sleeve, and which can be clamped through the intermediary of the inclined track against the shaft of the implement, which must be inserted into the recieving sleeve prior thereto for the purpose of implementing the clamping. It is the purpose of the known clamping arrangement to allow for the clamping of such shafts of dental implements which are differingly constructed in diameter as well in configurations. Hereby, this relates to so-called instruments or implements, the shafts of which can possess extremely different shapes for increasing their gripping strength.

It has been shown in actual practice, that the above-described purpose can only be partly fulfilled with the known clamping configuration. This is based on a number of reasons.

An important reason is that, in the vast majority of instances, there is only obtained a point like or punctiform contact between the spherical clamping element and the shaft which is to be clamped. As a consequence, the clamping of the shaft is rendered considerably more difficult, inasmuch as there are necessitated relatively larger forces in order to clamp the implement in the receiving sleeve so as to be secured against rotation.

A further deficiency of the known configuration resides in that the clamping element, in the presence of reductions or contractions in the shaft of the implement, must carry out relatively extensive radial adjusting movements in order to be able to come into contact with the associated contour of the shaft. As a result thereof, not only are there prescribed relatively extensive movements for the inclined track, but there is also required a relatively large force in order to radially displace the clamping element. At a manual displacement of the inclined track, this leads to a significant amount of work.

A further disadvantage is associated with the abovedescribed deficiency and in which the spherical or ball-shaped clamping element, upon abutting against the inclined surfaces of the implement shaft, produces relatively high axial force components on the shaft, as a result of which there are necessarily also produced relatively high axial supporting forces between the shaft and the receiving sleeve. This deficiency is prescribed by the ratio in size between the clamping element and a cutout present in the shaft, which must be considered as being unsatisfactory. It must be noted herein that any elimination of the above-described deficiencies through an increase in the size of the spherical clamping element, especially for handpieces, is not possible, inasmuch as this would lead to an increase in the overall dimensions, which should be avoided for handpieces.

SUMMARY OF THE INVENTION

It is an object of the present invention to eliminate the disadvantages of the above-mentioned arrangement by improving upon the effectiveness of the clamping arrangement while concurrently maintaining a small constructional size, in that the clamping element is formed by an elongated rod-shaped component which extends essentially axially or longitudinally within the clamping arrangement.

An important advantage of the inventive construction resides in that the clamping element, because of its elongated configuration will come into linear contact with cylindrical shafts, and for specially shaped shafts of the already mentioned implements, will in most instances come into two-pointed contact with the shaft. As a result there is obtained not only a low surface pressure at the contacting locations, but there can also be achieved a more effective clamping or gripping engagement, inasmuch as the shaft is retained at points which are spaced along its axial direction, as a result of which there is obtained a securer clamping because of a more expedient lever ratio. This is particularly applicable to such instances in which a plurality, preferably three, clamping elements are distributed about the circumference. In such a case, the inner wall of the receiving sleeve cannot be employed for supporting of the shaft when the latter is smaller dimensioned in diameter. As a result thereof, in such an instance the shaft of the known construction is merely supported in the area of an annular line at points corresponding to the number of clamping elements. In contrast therewith, the inventive construction facilitates a clamping at points which are spaced from each other in the longitudinal direction of the shaft.

A further advantage of the inventive construction resides in that the clamping element, because of its elongated or rod-shaped configuration, in contrast with the known construction, needs in most instances to traverse a shorter (radially inwardly directed) path until contacting the shaft. This path becomes shorter, the longer the dimensions of the clamping element. This advantage is predicated on that a rod-shaped clamping element is capable of at least partly bridging over cutouts or recesses present in the shaft.

Moreover, the inventive arrangement leads to the advantage that, because of the rod-shaped configuration and because of the capability of bridging over recesses which are present in the shaft, the clamping element produces lower axial force components on the shaft than is the case in the known construction.

Although, from the disclosure of German Pat. No. 905 528, there has become known a clamping arrangement of the type under consideration with rod-shaped clamping elements which extend longitudinally within the clamping arrangement, this known configuration does, however, basically differ from the inventive arrangement in that the surface of the inclined tracks extend in parallel with the longitudinal axis of the clamping arrangement, whereas in the inventive configuration, the surface of the inclined tracks extends perpendicular to the longitudinal axis of the clamping arrangement. Resulting therefrom is that the clamping elements of the known construction can only function along their axial orientation. In contrast therewith, the clamping element of the inventive arrangement can also provide clamping action in selective swivelled positions.

The clamping movement of the clamping element within the scope of the invention, can be produced by means of an inclined track which is inclined in the circumferential direction of the receiving sleeve, as well as by means of an axially adjustable inclined track.

In accordance with another embodiment of the invention, there is facilitated an optimum correlation between the clamping element and the configuration of the shaft, inasmuch as the clamping element is capable of being selectively swivelled about both of its end surfaces and thereby allows itself to be conformed.

Pursuant to another embodiment, the conforming of the end surfaces of the clamping element allows for lower loads acting on the contacting locations between the inclined track or tracks and the end surface or end surfaces of the clamping element.

Pursuant to another feature of the invention, there is obtained an advantageous support of the clamping element, in that it can be acted upon from the outside with the inclined track. Hereby, according to one embodiment, there is afforded that at a drawn out shaft, the clamping element or elements will not drop into the hollow space within the receiving sleeve.

Pursuant to another feature, because of reasons of obtaining a simpler configuration and arrangement, there is provided a clamping arrangement in which the movable inclined track is acted upon by a spring force in a direction towards the clamping element, so as not to require any manual effort in order to produce the clamping action. A manual effort is merely required for the release of the clamping arrangement, which, pursuant to a feature of the invention, can be achieved by acting upon a pressure element which, in the case of a handpiece with an angled headpiece, is located on the surface of the angled headpiece for easy manipulation, and which can be comfortably reached by the hand of the operator holding the handpiece.

Pursuant to further features of the invention, there is obtained a simple manufacture of the inclined tracks; and there are also provided the capabilities in that the clamped implement can be driven for the purpose of or oscillating rotation. Pursuant to another feature of the invention, the receiving sleeve is utilized as a rotational shaft.

Furthermore, the clamping arrangement allows for the conversion of a unidirectional rotation of the drive shaft into an oscillating rotational or swinging movement of the implement. For this purpose, in a simple manner, there can serve an eccentric cam on the drive shaft, which engages into a longitudinal groove in the receiving sleeve.

Furthermore, the arrangement may incorporate a drive mechanism in which the driving connection is automatically cut off when an overload or any other kind of difficulty should be encountered at the driven component of the mechanism. This is possible because the driving element, in essence the cam, of the drive mechanism can be displaced in opposition to the spring force from its engagement with the driven element.

BRIEF DESCRIPTION OF THE DRAWINGS

Reference may now be had to the following detailed description of preferred embodiments of the inventive clamping arrangement, taken in conjunction with the accompanying drawings; in which:

FIG. 1 illustrates a longitudinal view of an angled handpiece with an inventive clamping arrangement, and with an angled headpiece shown in action, into which there is clamped an implement;

FIG. 2 illustrates the clamping arrangement and the angled headpiece of FIG. 1, into which there is clamped an implement possessing a normal shaft;

FIG. 3 illustrates the implement of FIG. 1 in detail;

FIG. 4 illustrates the implement of FIG. 2 in detail;

FIG. 5 illustrates the clamping arrangement and angled headpiece according to FIGS. 1 and 2 on an enlarged scale, and with the implement having been omitted;

FIG. 6 illustrates a sectional view taken along line VI—VI in FIG. 5; and

FIG. 7 illustrates a detail of the clamping arrangement on an enlarged scale.

DETAILED DESCRIPTION

In the handpiece illustrated in FIG. 1, which is generally designated by reference numeral 1, because of reasons of simplicity, there is only illustrated the head sleeve 2 and a part of the gripping sleeve 3. The drive shaft parts 4, 5 and the angle drive 7 which is located in the region of the bending location 6, are illustrated only in phantom. The clamping arrangement is integrated in the angled headpiece 8 of the head sleeve 2 and; in essence, within a pickup or receiving sleeve 9 in which there is clamped an implement 11, and which is supported in a friction bearing in the angled headpiece 8 so as to be rotatable about the axis 12 of the implement 11, which can be oscillatingly driven by means of a connecting drive generally identified by reference numeral 13.

Essential elements of the clamping arrangement, which is generally identified by reference numeral 14, are the above-mentioned receiving sleeve 9, an adapter 15 which is arranged concentrically therein, three identical clamping elements 16 which are uniformly distributed over a part circle, and two inclined tracks 17, 18 which cooperate with the end surfaces 19, 21 of the clamping elements 16 in a manner as described hereinbelow.

The receiving sleeve 9 includes of an outer part 23, and an inner part which is formed by the adapter 15 which is supported so as to be axially displaceable within the outer part 23.

Of the two inclined tracks 17, 18, which are formed by mutually oppositely angled inclined or sloping surfaces 25, 26, the inclined track 17 which is distant from the tip 22 of the implement is formed on an inner surface (shoulder 20) of the receiving sleeve 9, whereas the inclined track 17 proximate the tip 22 of the implement is formed on the end surface of an annular shoulder 24 facing the inclined track 17, which is arranged on the adapter 15 and whose sloping surface 26 is formed by an annular surface.

The clamping elements 16 are configured rod-shaped, particularly cigar-shaped, and extend essentially along the axis 12. The end surfaces 19, 21 of the elements are somewhat rounded and thereby conformed to the sloping path of the inclined tracks 17, 18. The clamping elements 16 are located in radial cutouts 29 in the adapter 15 and in internal recesses 30 of the receiving sleeve 9 whose front-facing surfaces are, for instance, the conically-curved inclined or sloping tracks 17, 18. Consequently, the elements are in a position adapted to enter into the receiving space 31 for the shafts 27, 28. Hereby, the width of the cutouts 29 is somewhat narrower dimensioned than the diameter d of the clamping elements 16 which are round in cross-section, so that the clamping element cannot fall into the receiving space 31.

The clamping of the implement shafts 27, 28 is effected through the uniform radially by inward displacement of the clamping elements 16, which resultingly clamp the applicable shaft 27, 28 therebetween. The inward displacement of the clamping elements 16 is occasioned in that the inclined track 18 is displaced in the direction towards the inclined track 17, in view of which the clamping elements 16 are forced inwardly.

The clamping elements 16 can freely pivot in radial planes within the extent of their clearance between their inner and outer end positions, in effect, they can assume differently inclined or angled position relative to the axis 12 (shown by the double-headed arrow in FIG. 7). Consequently, they are in a position to conform to different shapes for the implement shafts 27, 28. Pursuant to FIG. 2, there is clamped in a normal implement 32 with a cylindrical shaft 28. Because of its rod-shaped form, the clamping elements 16 contact linearly against the gripping surface of the shaft 28.

In FIG. 1, there is shown clamped in an implement 11 possessing a shaft which is necked down for the purpose of increasing its grippability. It is clearly illustrated and recognizable, that the clamping elements 16 assume inclined positions with respect to the axis 12 with a two-point contact on shaft 27. Hereby, the inclined track 10 stands under the load of a compression spring 33, described below, which acts on the incline path 18 in direction towards the inclined track 17, and thereby also causes the clamping elements 16 to act against the shaft 27 (or 28). This resilient clamping force is adequate in order to centrally grip the shaft or the implement and to turn it upon rotation of the receiving sleeve.

An important advantage of the inventive construction resides of in that there is created an elastic clamping arrangement 14 which will spontaneously grip. Thus, no manual effort is required in order to move the clamping elements forwardly into a gripping direction. Hereby, the clamping arrangement 14 is in a position to centrally grip shafts possessing differently dimensioned diameters D.

The above-mentioned advantage is fully independent of the fact that the inventive construction is also exceedingly adapted to securely grip implements with specially configured shafts, such as implements 11, inasmuch as the clamping elements 16 can conform to the contour of the applicable gripping surface. Obtained therefrom is the further advantage that the shaft 27 is clamped in planes El, E2 which are oriented perpendicular to the shaft axis 12 and which are spaced from each other (spacing C). Consequently, the implement 11 is imparted a stable seating, whereby this seating is also afforded for such shafts whose diameter D is dimensioned smaller than the diameter D1 of the receiving space 29.

From FIG. 1 there can also be recognized that because the rod-shaped configuration of the clamping element 16, the recess in the shaft 27, which is identified by reference numeral 34, is partly bridged over, so that the path which is traversed by the clamping elements 16 until contact with the gripping surface, is in most instances less than the depth e of the recess 34.

A further advantage of the inventive arrangement also consists of in that the clamping elements 16, during gripping, are forced angled inwardly towards the side which is distant from the tip 22 of the implement. This movement is occasioned in that the inclined track 18 which is near the tip 22 of the implement is displaced in a direction towards the inclined track 17 which is located distant from the implement tip 22. The above-mentioned angling and the movement which is illustrated in FIG. 7 by arrow 35, leads to a drawing in action on the implement. As a result, the gripping engagement is imparted a further advantageous effect, inasmuch as through contact of the shafts 27, 28 against an inner stop 36, there can be further reinforced the seating of the implement in the gripped in position.

In FIG. 7, there is illustrated through "f" the difference between the outermost and innermost position of the illustrated clamping element 16 that there can be gripped implements with shafts 27, 28 whose diameter can have differentials up to two times.

The adapter 15 carries pressure element 37 at its end which is distant from the implement tip 22, which is insertable into a recess 38 in the angled headpiece 8 shaped in conformance with the external contour of the pressure element, wherein the compression spring 33 is clamped between this element 37 and the receiving sleeve 9 which is supported against a shoulder 39 in the angled headpiece 8. The compression spring 33 thus supports itself, by means of the receiving sleeve 9, in the angled headpiece 8, and clamps the pressure element 37 at a side distant from the implement tip 22. For the insertion and gripping engagement of the respective implement 32, 11; for example, there is slid in the pressure element 37 by means of one finger of the operator's hand holding the handpiece 1, as a result of which the clamping elements 16 are unclamped, and through the insertion of the shaft 27, 28 due to the conical reduction in their end surfaces 19, 21, are forced radially outwardly. In the inserted position of the pressure element 37, the implement 11, 32 can also be easily removed (shown by the phantom-line illustrated position of the adapter).

The connecting drive 13 encompasses an eccentric cam 41 of the drive shaft part 5 with roof-shaped sloped sides 42. The cam is fastened on a sleeve 43 which is arranged axially displaceably, but secured against rotation on the drive shaft part 5, and which is prestressed by a compression spring 44 in a direction towards the receiving sleeve 9. The receiving sleeve 9 along its includes a longitudinal groove 45 conformed with the V shape of the cam 41, which creates a locking connection between the cam 41 and the receiving sleeve 9. At a unidirectional rotation of the drive shaft part 5 and of the cam 41, the receiving sleeve 9 follows the movement of the cam 41, such that there is effected a conversion of the rotational movement of the cam 41 into an oscillating swinging movement of the receiving sleeve 9.

At an overloading of the implement 11, 32 or encountered difficulties in the receiving sleeve 9, the driving connection is automatically loosened. This is possible because of the longitudinally displaceable arrangement of the sleeve 43 carrying the cam 41, and because of the sloping extent of the flanks or sides 42. This, naturally, requires a suitable sizing of the spring force produced by the compression spring 44.

What is claimed is:

1. Clamping arrangement, especially for the gripping engagement of dental implements, comprising a handpiece; a receiving sleeve for a dental implement rotatably supported in said handpiece; a rotary drive connected with said receiving sleeve for imparting rotation thereto, said receiving sleeve including a cylindrical adapter having an inclined annular track surface at an end thereof remote from the tip of said dental implement, said adapter being axial displaceable; an annular shoulder supported by said receiving sleeve adjacent the opposite end of said adapter proximate the tip of said dental implement, said shoulder having an inclined annular track surface facing said track surface on said adapter; and a plurality of circumferentially spaced clamping elements oriented transversely of the longitudinal of said clamping arrangement such as to, upon contacting said inclined tracks, exert a radially inwardly acting pressure on a shaft of said implement which is inserted into said receiving sleeve, the improvement in that each of said clamping elements comprises a cylindrical rod-shaped member having rounded ends at the opposite ends thereof, said member extending in the direction of said clamping arrangement and having each rounded end contacting against respectively one of said inclined track surfaces; and spring means exerting an axial force on the adapter in a direction towards the tip of said dental implement for biasing said inclined track surface on said adapter in a direction towards the inclined track surface on said annular shoulder.

2. Clamping arrangement as claimed in claim 1 wherein the configuration of at least one of the end surfaces of each said clamping elements conforms with the shape of at least one of the inclined track surfaces.

3. Clamping arrangement as claimed in claim 1, wherein each said clamping elements traverse a cutout in adapter.

4. Clamping arrangement as claimed in claim 3, wherein the cutout has a smaller dimensioned inner edge than the axial cross-sectional dimension of the clamping elements.

5. Clamping arrangement as claimed in claim 1, wherein said handpiece has an angled headpiece, including an adjusting element associated with the displaceable inclined track surfaces, said adjusting element extending to the side of the angled headpiece which is distant from the tip of the implement.

6. Clamping arrangement as claimed in claim 5, wherein the adjusting element is constituted by said adapter.

7. Clamping arrangement as claimed in claim 5, wherein the adjusting element comprises a pressure element at the side of the angled headpiece which is distant from the tip of the implement.

8. Clamping arrangement as claimed in claim 7, wherein the spring is clamped between the pressure element and a part of the angled headpiece.

9. Clamping arrangement as claimed in claim 7, wherein the spring is supported on the receiving sleeve.

10. Clamping arrangement as claimed in claim 7, wherein the angled headpiece is covered by the adjusting element on the side of the headpiece facing away from the tip of the implement.

11. Clamping arrangement as claimed in claim 5, wherein the receiving sleeve is rotatably supported within the angled headpiece.

12. Clamping arrangement as claimed in claim 11, wherein the connecting drive imparts oscillating rotational movements to the receiving sleeve.

13. Clamping arrangement as claimed in claim 12, wherein a drive shaft of the connecting drive includes an eccentric cam which engages into an axial elongated groove formed in the receiving sleeve.

14. Clamping arrangement as claimed in claim 13, wherein said cam includes roof-shaped sloping sides, said sloping sides being substantially V-shaped to conform to the longitudinal groove, said cam being displaceably conducted in a guide along the drive shaft, and a spring for biasing the cam towards the longitudinal groove.

15. Clamping arrangement as claimed in claim 1 wherein said spring biases the displaceable inclined track surfaces on said adapter in a direction towards the clamping elements.

16. Clamping arrangement as claimed in claim 1 wherein the clamping elements are arranged main internal recess in the receiving sleeve, said recess being axially bounded by inclined track surprises.

* * * * *

UNITED STATES PATENT AND TRADEMARK OFFICE
CERTIFICATE OF CORRECTION

PATENT NO. : 4,781,589

DATED : November 1, 1988

INVENTOR(S) : Erich Bareth

It is certified that error appears in the above-identified patent and that said Letters Patent is hereby corrected as shown below:

Column 6, line 56: "its includes" should read as --its circumference includes"

Column 7, line 44, Claim 3: "in adapter" should read as --said adapter--

Column 8, line 45, Claim 16: "arranged main internal" should read as --arranged in an internal--

Column 8, line 47, Claim 16: "track surprises" should read as --track surfaces--

Signed and Sealed this

Twenty-eighth Day of November 1989

*Attest:*

JEFFREY M. SAMUELS

*Attesting Officer*     *Acting Commissioner of Patents and Trademarks*